(12) United States Patent
Hayakawa

(10) Patent No.: US 11,877,724 B2
(45) Date of Patent: Jan. 23, 2024

(54) INSERTION APPARATUS, AND DISTAL END MEMBER AND LID MEMBER OF INSERTION APPARATUS

(71) Applicant: OLYMPUS CORPORATION, Tokyo (JP)

(72) Inventor: Fumitoshi Hayakawa, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 827 days.

(21) Appl. No.: 16/943,080

(22) Filed: Jul. 30, 2020

(65) Prior Publication Data
US 2020/0352423 A1   Nov. 12, 2020

Related U.S. Application Data

(63) Continuation of application No. PCT/JP2018/030800, filed on Aug. 21, 2018.

(30) Foreign Application Priority Data

Jan. 31, 2018   (JP) ................. 2018-015056

(51) Int. Cl.
*A61B 1/00* (2006.01)
*A61B 1/018* (2006.01)
(Continued)

(52) U.S. Cl.
CPC ...... *A61B 1/00098* (2013.01); *A61B 1/00073* (2013.01); *A61B 1/00087* (2013.01);
(Continued)

(58) Field of Classification Search
CPC . A61B 1/00087; A61B 1/018; A61B 1/00098; A61B 1/00101; A61B 1/00073;
(Continued)

(56) References Cited

U.S. PATENT DOCUMENTS 5,569,157 A    10/1996   Nakazawa et al.
5,730,701 A *   3/1998   Furukawa .............. A61B 1/012
                                                                   600/129
(Continued)

FOREIGN PATENT DOCUMENTS

CN    102653324 A    9/2012
CN    205913157 U    2/2017
(Continued)

OTHER PUBLICATIONS

International Search Report dated Nov. 6, 2018 issued in PCT/JP2018/030800.

*Primary Examiner* — Timothy J Neal
(74) *Attorney, Agent, or Firm* — Scully, Scott, Murphy & Presser, P.C.

(57) ABSTRACT

A distal end member of an insertion apparatus includes: a base; a recessed portion which is recessed on a surface of the base; an opening forming surface formed on a surface of the base so as to surround a periphery of an opening of the recessed portion; and a lid member with a plate shape including a contact surface which is larger than the opening of the recessed portion and is brought into contact with the opening forming surface, the lid member closing the opening of the recessed portion by bringing the contact surface into contact with the opening forming surface. The lid member is formed so as to expose at least a portion of a side surface of the lid member disposed adjacently to the contact surface of the lid member to an outer surface of the base.

17 Claims, 8 Drawing Sheets

(51) Int. Cl.
 *A61B 1/04* (2006.01)
 *A61B 1/06* (2006.01)
(52) U.S. Cl.
 CPC .......... *A61B 1/018* (2013.01); *A61B 1/00091* (2013.01); *A61B 1/00165* (2013.01); *A61B 1/04* (2013.01); *A61B 1/06* (2013.01)
(58) Field of Classification Search
 CPC ......... A61B 1/04; A61B 1/00165; A61B 1/06; A61B 1/00096; A61B 1/00091; G02B 23/24
 See application file for complete search history.

(56) References Cited

U.S. PATENT DOCUMENTS

| | | | | |
|---|---|---|---|---|
| 2004/0082836 | A1* | 4/2004 | Hino | A61B 1/00142 |
| | | | | 600/107 |
| 2018/0092512 | A1 | 4/2018 | Hiraoka et al. | |
| 2018/0249894 | A1* | 9/2018 | Kolberg | A61B 1/00137 |
| 2021/0290042 | A1* | 9/2021 | Hosogoe | G02B 23/2476 |

FOREIGN PATENT DOCUMENTS

| | | | | | |
|---|---|---|---|---|---|
| CN | 107613880 | A | | 1/2018 | |
| EP | 3308715 | A1 | | 4/2018 | |
| JP | H02-040936 | A | | 2/1990 | |
| JP | H06-315458 | A | | 11/1994 | |
| JP | 2002-343949 | A | | 11/2002 | |
| JP | 2006-122327 | A | | 5/2006 | |
| JP | 2007-136044 | A | | 6/2007 | |
| JP | 2007136044 | A | * | 6/2007 | ......... A61B 1/00098 |
| TW | M263682 | U | | 5/2005 | |
| WO | WO 2016/199694 | A1 | | 12/2016 | |
| WO | WO-2016199694 | A1 | * | 12/2016 | ............... A61B 1/00 |

\* cited by examiner

INSERTION APPARATUS, AND DISTAL END MEMBER AND LID MEMBER OF INSERTION APPARATUS

CROSS REFERENCE TO RELATED APPLICATION

This application is a continuation application of PCT/JP2018/030800 filed on Aug. 21, 2018 and claims benefit of Japanese Application No. 2018-015056 filed in Japan on Jan. 31, 2018, the entire contents of which are incorporated herein by this reference.

BACKGROUND OF THE INVENTION

1. Field of the Invention

The present invention relates to an insertion apparatus which includes an insertion section, a recessed portion formed on the insertion section, and a lid member which covers the recessed portion, and a distal end member and the lid member of the insertion apparatus.

2. Description of the Related Art

As an insertion apparatus which has an insertion section inserted into a subject such as an endoscope or a medical treatment instrument, there has been known an insertion apparatus of a type which includes a movable member in the insertion section. For example, Japanese Patent Application Laid-Open Publication No. 2007-136044 discloses an endoscope where an insertion section includes an erecting lever and an erecting base which are movable members.

Japanese Patent Application Laid-Open Publication No. 2007-136044 discloses an endoscope where an erecting lever is disposed in a lever accommodating portion which is a space having a recessed shape formed in a distal end portion body of an insertion section. The endoscope disclosed in Japanese Patent Application Laid-Open Publication No. 2007-136044 is the endoscope where the lever accommodating portion is closed by a cover having a thin plate shape. The cover is fixed to the distal end portion body by an adhesive agent. The lever accommodating portion is a space which communicates with an inner space of the endoscope and hence, the cover which closes the lever accommodating portion is firmly fixed so as to prevent intrusion of a liquid.

SUMMARY OF THE INVENTION

An aspect of the present invention provides an insertion apparatus including: an insertion section configured to be inserted into a subject; a distal end member disposed on a distal end of the insertion section; a base forming the distal end member; a recessed portion formed on a surface of the base; an opening forming surface formed on a surface of the base so as to surround a periphery of an opening of the recessed portion; and a lid member with a plate shape, the lid member including a contact surface which is larger than the opening of the recessed portion and is brought into contact with the opening forming surface, the lid member being configured to close the opening of the recessed portion by bringing the contact surface into contact with the opening forming surface. The lid member is formed so as to expose at least a portion of a side surface of the lid member disposed adjacently to the contact surface of the lid member to an outer surface of the base, and at a portion of a corner of the lid member where the contact surface and the side surface which is exposed to an outside intersect with each other, an opening portion is formed by cutting out the corner.

Another aspect of the present invention provides a distal end member of an insertion apparatus. The distal end member is disposed on a distal end of an Insertion section inserted into a subject, and includes: a base; a recessed portion formed on a surface of the base; an opening forming surface formed on a surface of the base so as to surround a periphery of an opening of the recessed portion; and a lid member with a plate shape, the lid member including a contact surface which is larger than the opening of the recessed portion and is brought into contact with the opening forming surface, the lid member being configured to close the opening of the recessed portion by bringing the contact surface into contact with the opening forming surface. The lid member is formed so as to expose at least a portion of a side surface of the lid member disposed adjacently to the contact surface of the lid member to an outer surface of the base, and at a portion of a corner of the lid member where the contact surface and the side surface which is exposed to an outside intersect with each other, an opening portion is formed by cutting out the corner.

Another aspect of the present invention provides a lid member with a plate shape. The lid member is configured to close an opening of a distal end member which is disposed on an insertion section inserted into a subject, the distal end member including a base, a recessed portion formed on a surface of the base, and an opening forming surface formed on a surface of the base so as to surround a periphery of an opening of the recessed portion. The lid member is formed so as to expose at least a portion of a side surface of the lid member disposed adjacently to a contact surface of the lid member which is brought into contact with the opening forming surface to an outer surface of the base, and at a portion of a corner of the lid member where the contact surface and the side surface which is exposed to an outside intersect with each other, an opening portion is formed by cutting out the corner.

DETAILED DESCRIPTION OF THE PREFERRED EMBODIMENT

Hereinafter, a preferred embodiment of the present invention is described with reference to drawings. In the respective drawings used in the description made hereinafter, to set sizes of the respective constitutional elements to a degree that allows the respective constitutional elements recognizable on the drawings, there may be a case where the scale is made different for respective constitutional elements. The present invention is not limited only to the number of constitutional elements, shapes of the constitutional elements, ratios between sizes of the constitutional elements, and the relative positional relationship between the respective constitutional elements described in these drawings.

Figure 1:
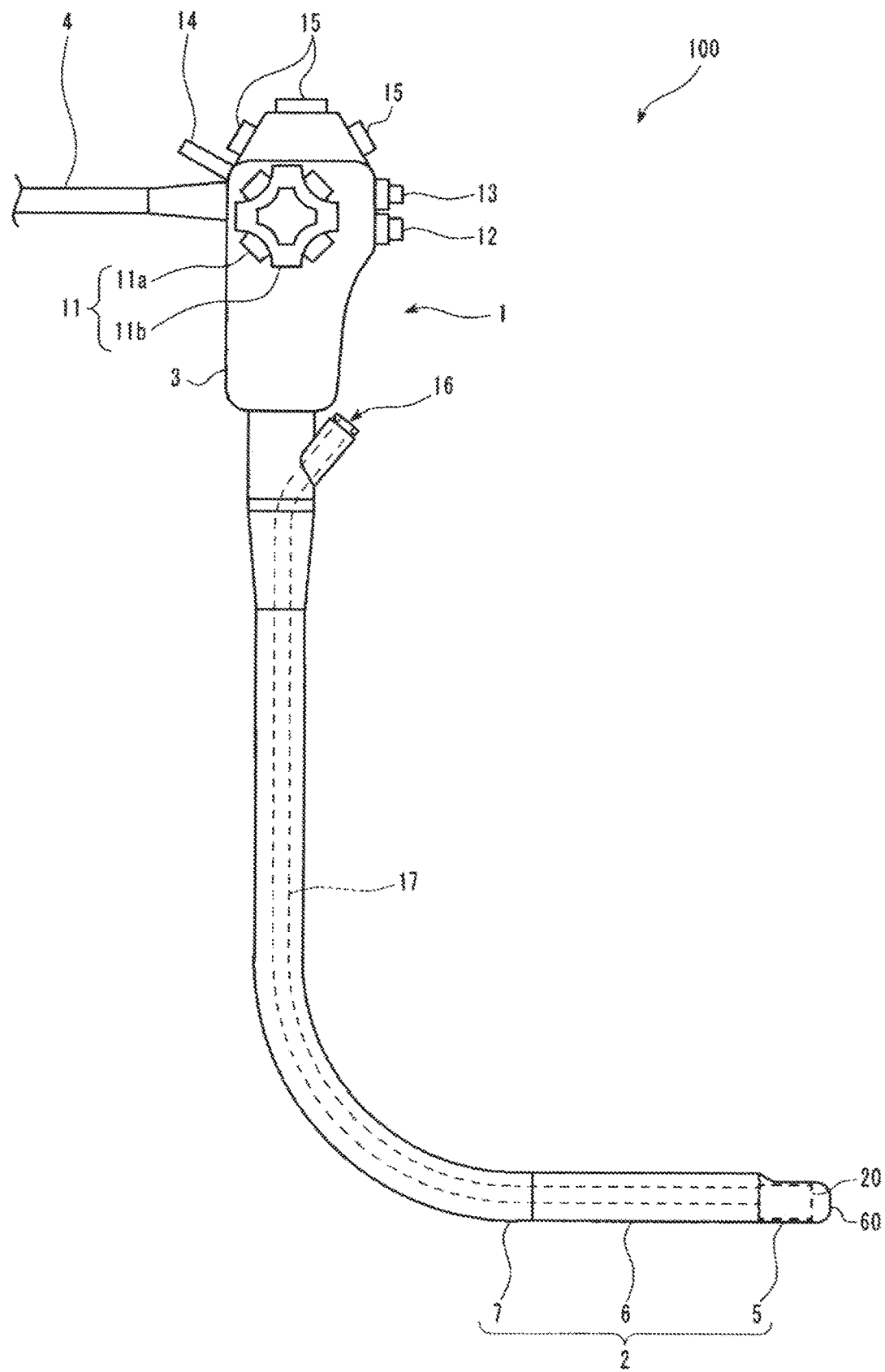
FIG. 1 a view showing a schematic configuration of an insertion apparatus.

FIG. 1 is a view showing a schematic configuration of an insertion apparatus 100. The insertion apparatus 100 of the present embodiment includes an insertion apparatus body 1 and a distal end cover 60. In the present embodiment, as one example, the insertion apparatus 100 is an endoscope which has an insertion section 2 inserted into a human body which is a subject. More specifically, the insertion apparatus 100 is a side-viewing endoscope for intestine duodenum.

The insertion apparatus body 1 is formed of: the insertion section 2 which is inserted into a subject; an operation section 3 which is mounted on a proximal end side of the insertion section 2; and a universal cord 4 which extends from the operation section 3.

A bending operation device 11, an air/water feeding button 12, a suction button 13, a raising base operation lever 14, and operation switches 15 are mounted on the operation section 3. The operation switches 15 are electronic switches for operating an image pickup apparatus 42 (not shown in FIG. 1) mounted on the insertion section 2.

A treatment instrument insertion opening 16 through which a treatment instrument not shown is introduced into a human body is formed in the operation section 3. A proximal end side of a channel tube 17 is connected to the treatment instrument insertion opening 16. A distal end side of the channel tube 17 opens at a distal end portion 5 of the insertion section 2.

The insertion section 2 is formed by connecting: the distal end portion 5 which is disposed on a distal end of the insertion section 2; a bending portion 6 which is bendable and is disposed on a proximal end side of the distal end portion 5; and a flexible tube portion 7 which has flexibility and connects a proximal end side of the bending portion 6 and the operation section 3 to each other. The distal end cover 60 is mounted on the distal end portion 5. The configurations of the distal end portion 5 and the distal end cover 60 are described in detail later.

The bending portion 6 bends in an upward direction or in a downward direction corresponding to a rotation of a vertical bending knob 11a of the bending operation device 11 mounted on the operation section 3, and the bending portion 6 bends in a leftward direction or in a rightward direction corresponding to a rotation of a lateral bending knob 11b of the bending operation device 11.

A raising base operation wire 18 (not shown in FIG. 1) passes through the insertion section 2. The raising base operation wire 18 advances or retracts in a longitudinal direction corresponding to swinging of the raising base operation lever 14. In other words, the raising base operation lever 14 is an operation member with which a user operates a device for pushing or pulling the raising base operation wire 18 passed through inside the insertion section 2. A distal end of the raising base operation wire 18 is connected to a movable member 51 described later (not shown in FIG. 1) which is mounted on the distal end portion 5.

Figure 2:
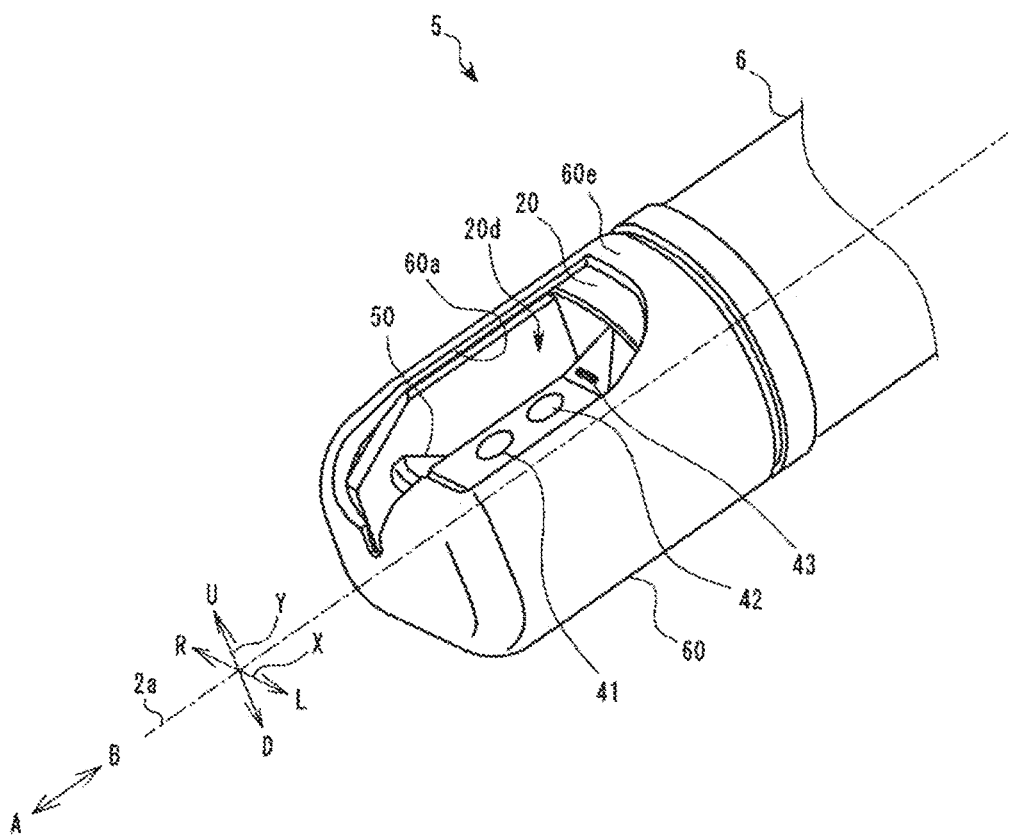
FIG. 2 is a perspective view of a distal end portion of an insertion section.
Figure 3:
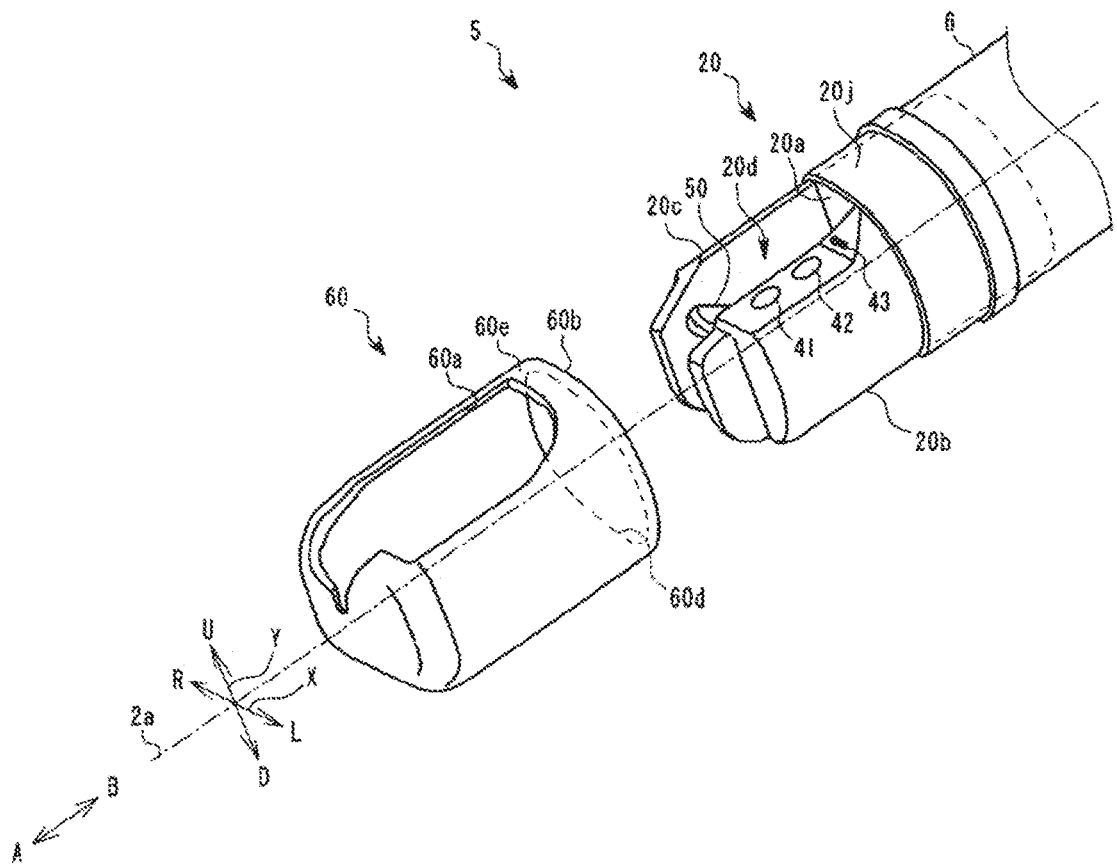
FIG. 3 is a perspective view showing a state where a distal end cover and a distal end member are separated from each other.
Figure 4:
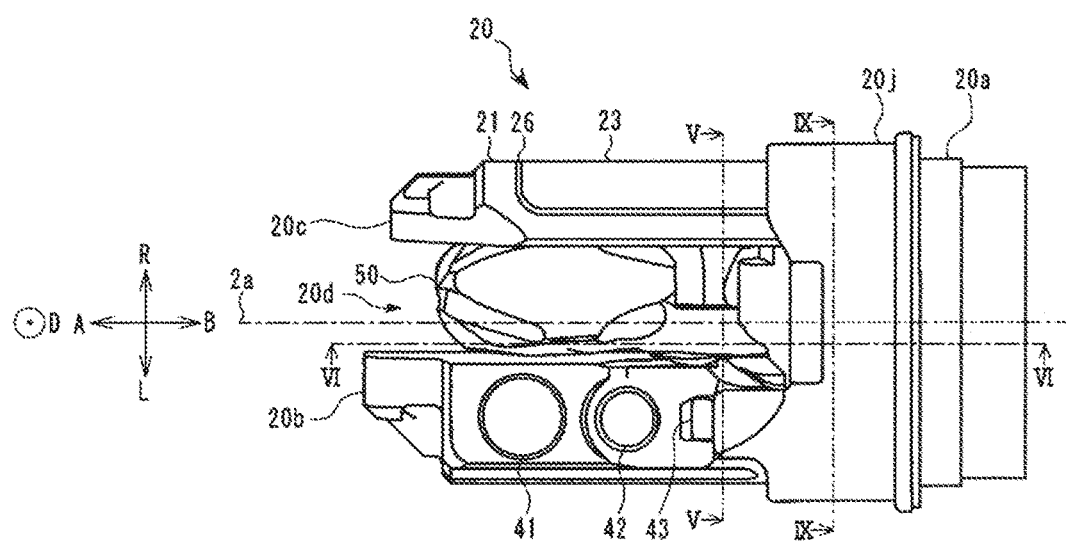
FIG. 4 is a view showing an upper surface of the distal end member.
Figure 5:
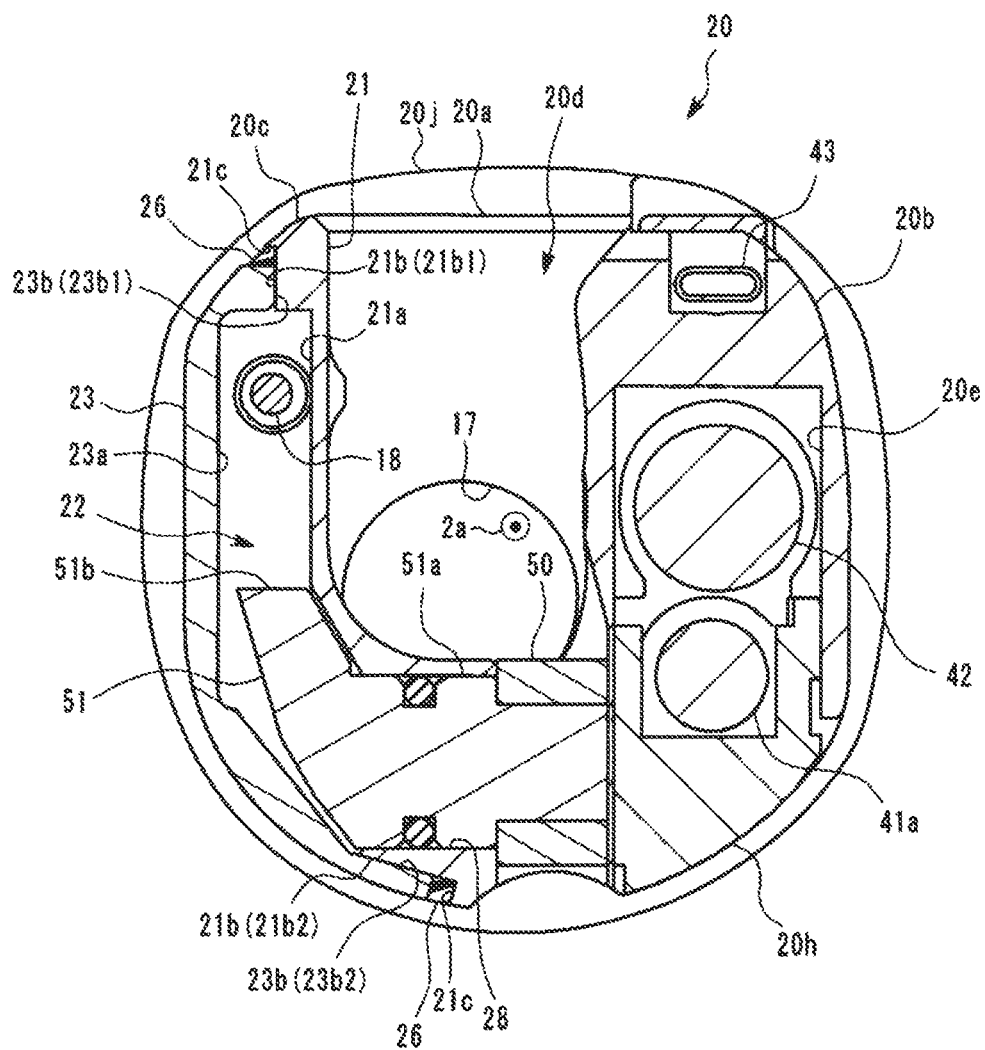
FIG. 5 is a cross-sectional view taken along line V-V in FIG. 4.
Figure 5:
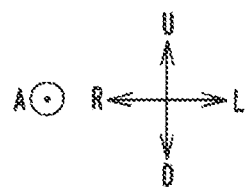
Figure 6:
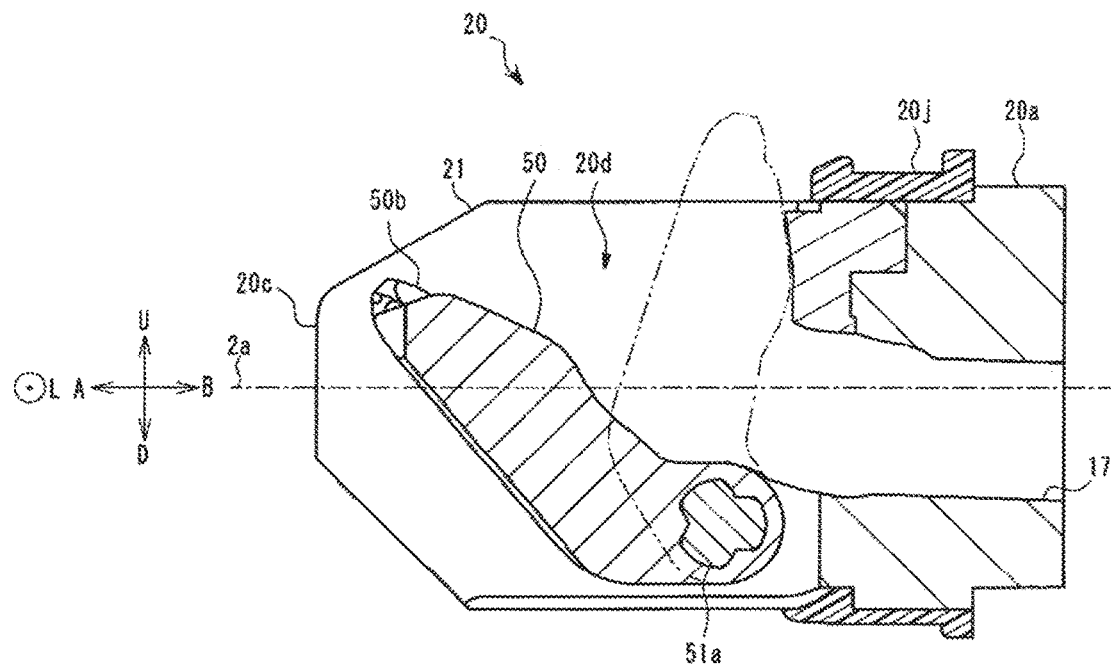
FIG. 6 is a cross-sectional view taken along line VI-VI in FIG. 4.
Figure 7:
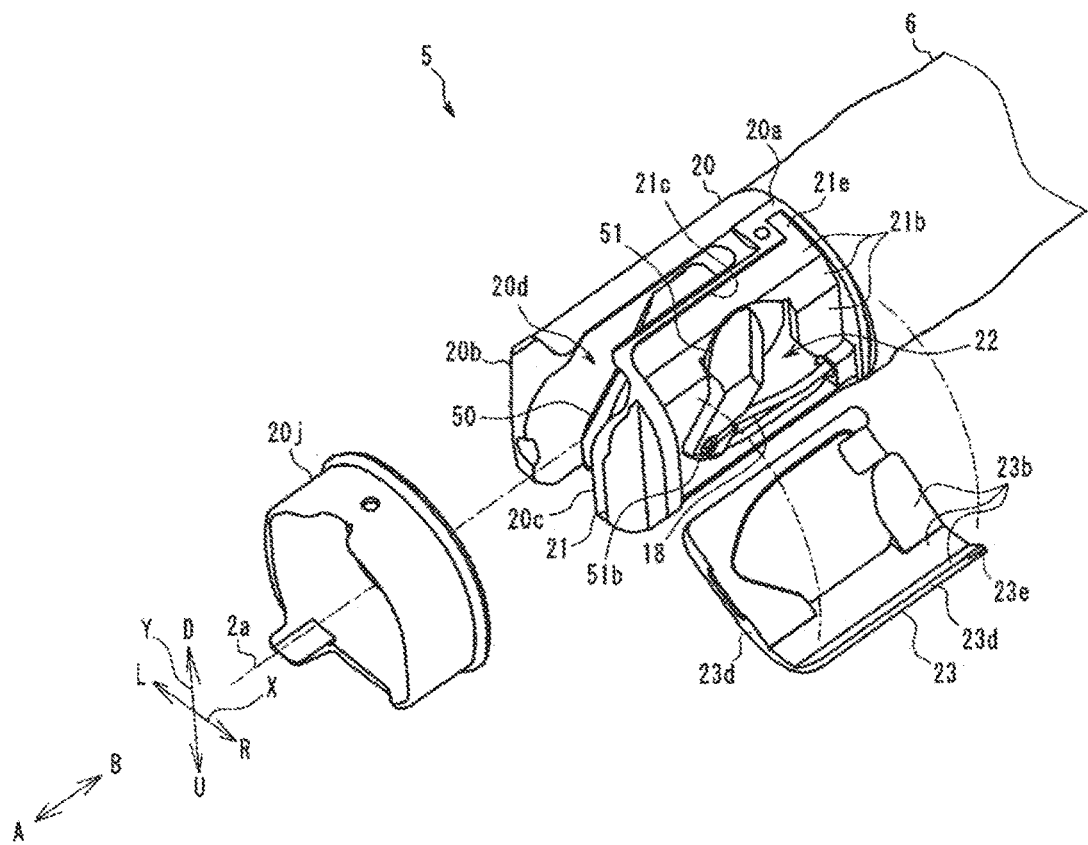
FIG. 7 is an exploded perspective view of the distal end member.
Figure 8:
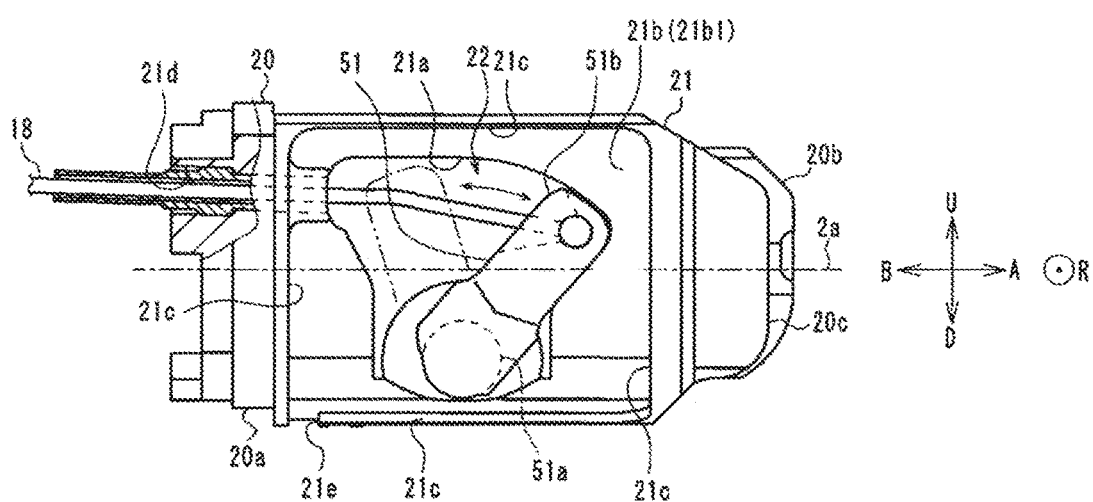
FIG. 8 is a view showing a right side surface of the distal end member in a state where a lid member is removed from the distal end member.

FIG. 2 is a perspective view of the distal end portion 5. As shown in FIG. 2, the distal end cover 60 is mounted on the distal end portion 5. The distal end cover 60 is a sheath-shaped member which covers a predetermined outer surface of the distal end portion 5, and is detachably mounted on the distal end portion 5. FIG. 3 is a perspective view showing a state where the distal end cover 60 and the distal end portion 5 are separated from each other. FIG. 4 is a view showing an upper surface of the distal end portion 5 in a state where the distal end cover 60 is not mounted on the distal end portion 5. FIG. 5 is a cross-sectional view taken along line V-V in FIG. 4. FIG. 6 is a cross-sectional view taken along line VI-VI in FIG. 4. FIG. 7 is an exploded perspective view of a distal end member 20. FIG. 8 is a view showing a right side surface of the distal end member 20 in a state where a lid member 23 is removed from the distal end member 20.

In the present embodiment, as one example, the distal end cover 60 is formed using a resin which has low elasticity compared to rubber or the like and is easily plastically deformable and breakable among resins such as polyethylene or polypropylene. In the present embodiment, the distal end cover 60 is formed such that irreversible deformation or breaking occurs in the distal end cover 60 when the distal end cover 60 is removed from the distal end portion 5 after the distal end cover 60 is mounted on the distal end portion 5. Accordingly, the distal end cover 60 cannot be reused. FIG. 3 shows the distal end cover 60 in a state where the distal end cover 60 has not ever been mounted on the distal end portion 5 (unused state).

The configuration of the distal end portion 5 is described. In the description made hereinafter, an axis which extends in a longitudinal direction of the elongated insertion section 2 is referred to as a longitudinal axis 2a. A direction directed toward a distal end side of the insertion section 2 along the longitudinal axis 2a is referred to as a distal end direction A, and a direction opposite to the distal end direction A is referred to as a proximal end direction B. Two straight line axes which are orthogonal to each other on a plane orthogonal to the longitudinal axis 2a are defined as an X axis and a Y axis respectively. A direction directed toward one side along the X axis is referred to as a rightward direction R, and a direction opposite to the rightward direction R is referred to as a leftward direction L. A direction directed toward one side along the Y axis is referred to as an upward direction U, and a direction opposite to the upward direction U is referred to as a downward direction D. The X axis and the Y axis are substantially parallel to a bending direction of the bending portion 6. In the present embodiment, as one example, in a case where the distal end portion 5 is viewed from a proximal end side toward a distal end side along the longitudinal axis 2a, and the X axis is taken horizontally, assume a right side as the rightward direction R and an upper side as the upward direction U.

As shown in FIG. 3, the distal end portion 5 includes the distal end member 20 and an insulation portion 20j. The distal end member 20 has: a proximal portion 20a which is fixed to a distal end of the bending portion 6; a first arm portion 20b and a second arm portion 20c which form a pair of arm portions projecting from the proximal portion 20a in the distal end direction A; and a raising base accommodating space 20d which is a space formed between the first arm portion 20b and the second arm portion 20c. The proximal portion 20a has a substantially columnar profile.

The insulation portion 20j is an annular member which covers an outer periphery of the proximal portion 20a. The insulation portion 20j is made of a resin or ceramic having electric insulation property.

The first arm portion 20b and the second arm portion 20c of the distal end member 20 are disposed such that the raising base accommodating space 20d which is the space formed between the first arm portion 20*b* and the second arm portion 20*c* opens in three directions including the upward direction U, the downward direction D, and the distal end direction A. In other words, the first arm portion 20*b* and the second arm portion 20*c* are arranged in a direction along the X axis with the raising base accommodating space 20*d* sandwiched between the first arm portion 20*b* and the second arm portion 20*c*. In the present embodiment, as one example, the first arm portion 20*b* is disposed on a leftward direction L side of the raising base accommodating space 20*d*, and the second arm portion 20*c* is disposed on a rightward direction R side of the raising base accommodating space 20*d*.

On an upper surface of an outer peripheral surface of the first arm portion 20*b* facing in the upward direction U, an illumination lens 41, the image pickup apparatus 42, and a cleaning nozzle 43 are disposed. The illumination lens 41 is provided for irradiating illumination light toward an object, an image of which is picked up by the image pickup apparatus 42.

As shown in FIG. 5, an image pickup apparatus accommodating chamber 20*e* is formed in the first arm portion 20*b*. A distal end portion of an optical fiber cable 41*a* and the image pickup apparatus 42 are disposed in the image pickup apparatus accommodating chamber 20*e*. The optical fiber cable 41*a* passes through the insertion section 2, and guides an illumination light irradiated from a light emitting device to the illumination lens 41.

A field of view of the image pickup apparatus 42 is defined with the substantially upward direction U set as the center of the field of view. In other words, the image pickup apparatus 42 embraces a side of the insertion section 2 in the field of view. The cleaning nozzle 43 is a part which ejects a fluid toward the illumination lens 41 and the image pickup apparatus 42.

An accommodating chamber 22 in which the movable member 51 is disposed is formed in the second arm portion 20*c*. The movable member 51 is a member which transmits the movement of the raising base operation wire 18 to a raising base (forceps elevator) 50.

As shown in FIG. 5, a bearing 28 which rotatably supports a shaft portion 51*a* fixed to a movable member 51 is disposed in the second arm portion 20*c*. A rotation axis of the shaft portion 51*a* is substantially parallel to the X axis. The shaft portion 51*a* extends in a penetrating manner from the accommodating chamber 22 to the raising base accommodating space 20*d*.

As shown in FIG. 8, the movable member 51 includes a lever 51*b* which is disposed in the accommodating chamber 22 and extends in a direction orthogonal to the shaft portion 51*a*. The accommodating chamber 22 communicates with the inside of the bending portion 6 through a through hole 21*d*. The through hole 21*d* penetrates the proximal portion 20*a* from an inside of the accommodating chamber 22 in the proximal end direction B. The raising base operation wire 18 passes through the through hole 21*d*. A distal end of the raising base operation wire 18 is connected to the lever 51*b* at a position away from the shaft portion 51*a* by a predetermined distance.

As described previously, the raising base operation wire 18 advances or retracts in the longitudinal direction corresponding to swinging of the raising base operation lever 14. Along with advancing or retracting of the raising base operation wire 18, the movable member 51 rotates about the rotation axis.

The raising base 50 is fixed to a portion of the shaft portion 51*a* which projects into the raising base accommodating space 20*d*. As shown in FIG. 6, the raising base 50 rotates in the raising base accommodating space 20*d* along with the rotation of the movable member 51.

The raising base 50 is a tongue-shaped member which extends in one direction from the shaft portion 51*a*. In the raising base accommodating space 20*d*, the treatment instrument channel tube 17 has an opening at a proximal end direction B side of the raising base 50. Along with swinging of the raising base 50, an angle of the treatment instrument which projects from the treatment instrument channel tube 17 changes.

As shown in FIG. 3, the distal end cover 60 is a sheath-shaped member where a distal end direction A side is closed and a proximal end direction B side is opened. An opening formed on the proximal end direction B side of the distal end cover 60 is referred to as an insertion opening 60*d*. In mounting the distal end cover 60 on the distal end portion 5, the distal end portion 5 is inserted in the distal end cover 60 through the insertion opening 60*d*.

The distal end cover 60 has an opening portion 60*a* through which the raising base accommodating space 20*d* is exposed only in the upward direction U in a state where the distal end cover 60 is mounted on the distal end portion 5. The illumination lens 41, the image pickup apparatus 42, and the cleaning nozzle 43 are also exposed in the upward direction U through the opening portion 60*a* in the state where the distal end cover 60 is mounted on the distal end member 20.

On an outer surface of the distal end cover 60, the opening portion 60*a* is not connected with the insertion opening 60*d*. Accordingly, an annularly continuous annular portion 60*e* is formed on a proximal end 60*b* of the distal end cover 60 over the whole circumference about the longitudinal axis 2*a*. In the state where the distal end cover 60 is mounted on the distal end member 20, the annular portion 60*e* engages with an outer periphery of the insulation portion 20*j* by fitting.

Figure 9:
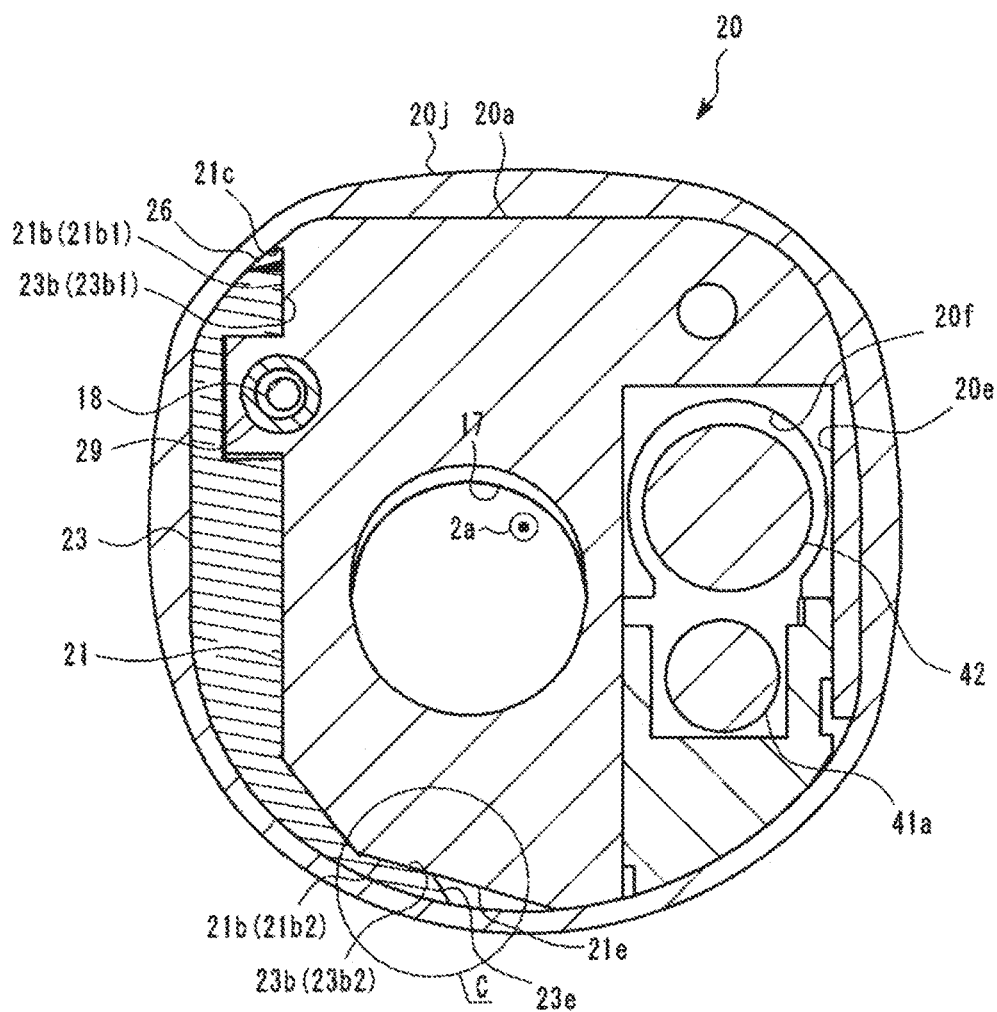
FIG. 9 is a cross-sectional view taken along line IX-IX in FIG. 4.
Figure 9:
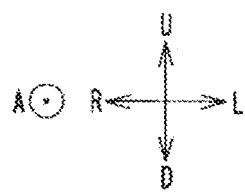
Figure 10:
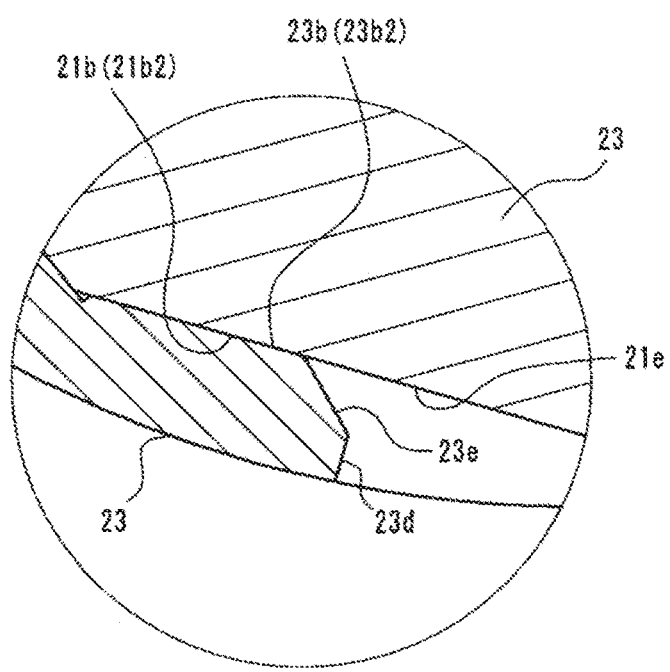
FIG. 10 is an enlarged view of a portion in FIG. 9 surrounded by a circle C.

Next, a configuration of the accommodating chamber 22 formed in the second arm portion 20*c* of the distal end member 20 is described. FIG. 9 is a cross-sectional view taken along line IX-IX in FIG. 4. FIG. 10 is an enlarged view of a portion in FIG. 9 surrounded by a circle C.

As shown in FIG. 4, FIG. 5, and FIG. 7, the second arm portion 20*c* is formed of a base portion 21 which is integrally formed with the distal end member 20, and the lid member 23 which is fixed by adhesion to the base portion 21 using a fixing resin 26. In the present embodiment, the lid member 23 is fixed to a right side surface (the rightward direction R side in FIG. 4) of the base portion 21. The accommodating chamber 22 is a space surrounded by an inner surface of a recessed portion 21*a* formed on the base portion 21 and an inner surface of the lid member 23 which covers the recessed portion 21*a*.

More specifically, the base portion 21 has the recessed portion 21*a*, an opening forming surface 21*b*, and a wall surface portion 21*c*. The recessed portion 21*a* opens on a surface of the base portion 21 within the opening forming surface 21*b*. In other words, the opening forming surface 21*b* is a surface formed so as to surround a periphery of an opening of the recessed portion 21*a*.

The shape of the opening forming surface 21*b* is not particularly limited, and the opening forming surface 21*b* may be formed of a single planar surface, for example. Alternatively, the opening forming surface 21*b* may be formed of a plurality of planar surfaces or a curved surface.

In the present embodiment, as one example, as shown in FIG. 5 and FIG. 9, the opening forming surface 21*b* includes a pair of planar surfaces 21*b*1 and 21*b*2 which is arranged substantially parallel to the longitudinal axis 2a at an angle that the planar surfaces 21b1 and 21b2 intersect with each other. The pair of planar surfaces 21b1 and 21b2 faces in different directions on a surface of the base portion 21 having a columnar shape such that an intersecting line of the planar surfaces 21b1 and 21b2 forms a ridge line projecting toward the outside.

The opening forming surface 21b which includes the pair of planar surfaces 21b1 and 21b2 is formed in a crest bent shape in cross section orthogonal to a longitudinal axis 2a.

The wall surface portion 21c is raised from the opening forming surface 21b toward the outside of the base portion 21. The wall surface portion 21c is described later.

The lid member 23 is a member with a plate shape, and includes a contact surface 23b. The contact surface 23b is a surface which is brought into contact with the opening forming surface 21b. The contact surface 23b is larger than an opening of the recessed portion 21a, and is brought into contact with the opening forming surface 21b over an entire periphery of the opening of the recessed portion 21a. Accordingly, the opening of the recessed portion 21a is closed by the lid member 23 in a state where the contact surface 23b is brought into contact with the opening forming surface 21b.

The contact surface 23b is formed in a shape which allows the contact surface 23b to be brought into close contact with the opening forming surface 21b for closing the recessed portion 21a. More specifically, in the present embodiment, the opening forming surface 21b is formed in a crest shape in cross section parallel to the longitudinal axis 2a and hence, the contact surface 23b has a valley shape in conformity with bending of the opening forming surface 21b. In other words, the contact surface 23b has a pair of planar surfaces 23b1 and 23b2 which is parallel to the pair of planar surfaces 21b1 and 21b2 of the opening forming surface 21b.

In this manner, the opening forming surface 21b on a base portion 21 side is formed in a crest shape, and the contact surface 23b on the lid member 23 side is formed in a valley shape. Accordingly, by bringing the contact surface 23b into contact with the opening forming surface 21b, the lid member 23 is positioned with respect to the base portion 21 in a circumferential direction about the longitudinal axis 2a. In the present embodiment, positioning of the lid member 23 with respect to the base portion 21 in the circumferential direction about the longitudinal axis 2a is the positioning of the lid member 23 in the upward direction U and the downward direction D substantially along the Y axis.

The wall surface portion 21c formed on the base portion 21 is raised from the opening forming surface 21b toward the outside of the base portion 21. The wall surface portion 21c has a surface which faces at least a portion of the side surface 23d of the lid member 23 in a state where the contact surface 23b is brought into contact with the opening forming surface 21b.

In the present embodiment, the wall surface portion 21c is disposed so as to surround a periphery of the lid member 23 in a spaced-apart manner from the side surface 23d by a predetermined distance. In other words, in the present embodiment, the wall surface portion 21c forms a side wall surface of a recessed portion which is formed on a surface of the base portion 21 and is formed in a shape which allows the lid member 23 to be fitted in the recessed portion, and the opening forming surface 21b forms a bottom surface of the recessed portion.

An end surface of the wall surface portion 21c forms an outer surface of the distal end member 20. The lid member 23 is fixed by adhesion to the base portion 21 by pouring a fixing resin 26 which is not yet cured between the lid member 23 and the wall surface portion 21c and, thereafter, by curing the fixing resin 26. As shown in FIG. 4, an outer surface of the lid member 23 and an outer surface of the fixing resin 26 are formed so as to be coplanar with an outer surface of the distal end member 20.

In the present embodiment, in the distal end member 20 of the insertion apparatus 100, the periphery of the lid member 23 is surrounded by the wall surface portion 21c, and the fixing resin 26 is disposed so as to surround an entire periphery of the lid member 23. Accordingly, a fixing strength for fixing the lid member 23 can be enhanced.

In the present embodiment, as shown in FIG. 7, FIG. 9 and FIG. 10, a cutout 21e is formed in a portion of the wall surface portion 21c by cutting out the wall surface portion 21c to the opening forming surface 21b. Though the cutout 21e, a portion of the side surface 23d disposed adjacently to the contact surface 23b of the lid member 23 is exposed to an outer surface of the base portion 21. As shown in FIG. 4 and FIG. 5, the cutout 21e is covered by the insulation portion 20j in a state where the distal end member 20 is assembled.

The side surface 23d of the lid member 23 is surrounded by the wall surface portion 21c formed on the base portion 21. However, at a portion of the side surface 23d where the cutout 21e is formed the side surface 23d can be observed from the outside of the distal end member 20 by removing a fixing resin 26 disposed in the portion where the cutout 21e is formed.

More specifically, at the cutout 21e formed in the wall surface portion 21c, a boundary between the lid member 23 and the base portion 21 is exposed on the outer surface of the base portion 21. The boundary between the lid member 23 and the base portion 21 is a portion where the opening forming surface 21b and the contact surface 23b are brought into contact with each other.

In this manner, in the insertion apparatus of the present embodiment, at the portion of the wall surface portion 21c where the cutout 21e is formed, after the fixing resin 26 disposed at such a portion is removed, it is possible to expose the portion where the opening forming surface 21b and the contact surface 23b are brought into contact with each other to the outside of the distal end member 20.

Accordingly, in the distal end member 20 of the insertion apparatus 100 of the present embodiment, by removing the fixing resin 26 disposed at the portion where the cutout 21e is formed, a tool having a thin plate shape or a wedge shape can be inserted at the portion where the opening toning surface 21b and the contact surface 23b are brought into contact with each other. Further, as described previously, in the distal end member 20 of the present embodiment, by arranging the fixing resin 26 such that the fixing resin 26 surrounds the entire periphery of the lid member 23, the fixing strength for fixing the lid member 23 can be enhanced. Accordingly, in the distal end member 20 of the insertion apparatus 100 of the present embodiment, the fixing strength for fixing the lid member 23 which closes the recessed portion 21a can be maintained. Furthermore, at the time of removing the lid member 23, the lid member 23 can be easily removed.

Further, in the present embodiment, as shown in FIG. 7, FIG. 9 and FIG. 10, in the vicinity of the portion of the wall surface portion 21c where the cutout 21e is formed, at a portion of a corner of the lid member 23 where the contact surface 23b and the side surface 23d intersect with each other, an opening portion 23e is formed by cutting out the corner.

The opening portion 23e has a so-called chamfered shape. The chamfered shape is formed by cutting out the corner of the lid member 23 at an angle by which the opening portion 23e intersects with the opening forming surface 21b at an acute angle. The opening portion 23e forms a space having a wedge shape which extends toward the recessed portion 21a along the boundary between the lid member 23 and the base portion 21.

In such a present embodiment, at the portion of the wall surface portion 21c where the cutout 21e is formed, by removing the fixing resin 26 disposed in the portion, the portion of the lid member 23 where the opening portion 23e is formed is exposed to the outer surface of the base portion 21. In the distal end member 20 of the present embodiment, by inserting a tool having a thin plate shape or a wedge shape into the opening portion 23e, it is possible to easily apply a force to the lid member 23 in a direction for peeling off the lid member 23 from the opening forming surface 21b. Accordingly, the lid member 23 can be easily removed.

The opening portion 23e may be a groove which allows the portion of the corner where the contact surface 23b and the side surface 23d of the lid member 23 intersect with each other to be positioned away from the opening forming surface 21b by carving a portion of the opening forming surface 21b of the base portion 21.

The present invention is not limited to the above-mentioned embodiment, and can be suitably modified without departing from the gist or the technical concept of the invention which are conceivable from claims and the entire specification, and the distal end member of the insertion apparatus which includes such modifications also falls within the technical scope of the present invention.

What is claimed is:

1. An insertion apparatus comprising:
    an insertion section configured to be inserted into a subject;
    a distal end member having a base disposed on a distal end of the insertion section;
    a recess formed in the base, the base having an opening forming surface surrounding a periphery of the recess, the periphery of the recess defining an opening; and
    a lid including a contact surface larger than the opening of the recess, the contact surface contacts a first portion of the opening forming surface when the lid is arranged to close the opening of the recess,
    wherein a gap is formed when the lid is arranged to close the opening of the recess, the gap being formed between an outer peripheral edge of the lid and a second portion of the opening forming surface adjacent to the outer peripheral edge of the lid.

2. The insertion apparatus according to claim 1, wherein the insertion section is configured to be inserted into a lumen of a subject.

3. The insertion apparatus according to claim 1, wherein the outer peripheral edge of the lid member has an angled surface formed at an acute angle.

4. The insertion apparatus according to claim 1, wherein the outer peripheral edge comprises a chamfer at least partially forming the gap.

5. The insertion apparatus according to claim 1, further comprising a fixing resin disposed in the gap for adhering the lid to the base.

6. The insertion apparatus according to claim 5, wherein an outer surface of the fixing resin is coplanar with an outer surface of the base.

7. The insertion apparatus according to claim 1, wherein the insertion apparatus is an endoscope.

8. The insertion apparatus according to claim 1, wherein the gap having a wedge shape extending toward the recess along a boundary between the lid and the base.

9. A distal end member of an insertion apparatus which is disposed on a distal end of an insertion section configured to be inserted into a subject, the distal end member of the insertion apparatus comprising:
    a base;
    a recess formed of in the base, the base having an opening forming surface surrounding a periphery of the recess, the periphery of the recess defining an opening; and
    a lid including a contact surface larger than the opening of the recess, the contact surface contacts a first portion of the opening forming surface when the lid is arranged to close the opening of the recess,
    wherein a gap is formed when the lid is arranged to close the opening of the recess, the gap being formed between an outer peripheral edge of the lid and a second portion of the opening forming surface adjacent to the outer peripheral edge of the lid.

10. The distal end member of an insertion apparatus according to claim 9, wherein the outer peripheral edge of the lid member has an angled surface formed at an acute angle.

11. The distal end member of an insertion apparatus according to claim 9, wherein the outer peripheral edge comprises a chamfer at least partially forming the gap.

12. The distal end member of an insertion apparatus according to claim 9, further comprising a fixing resin disposed in the gap for adhering the lid to the base.

13. The distal end member of an insertion apparatus according to claim 12, wherein an outer surface of the fixing resin is coplanar with an outer surface of the base.

14. The insertion apparatus according to claim 9, wherein the gap having a wedge shape extending toward the recess along a boundary between the lid and the base.

15. A lid configured to close an opening in a base of a distal end member disposed on an insertion section configured to be inserted into a subject, a recess formed in the base, the base having an opening forming surface surrounding a periphery of the recess, the periphery of the recess defining the opening, the lid comprising:
    a lid member is formed so as to expose at least a portion of an outer peripheral edge of the lid member disposed adjacently to a portion of the opening forming surface, and
    the outer peripheral edge of the lid member forming a gap with the portion of the opening forming surface adjacent to the outer peripheral edge.

16. The lid member according to claim 15, wherein the the outer peripheral edge has an angled surface formed at an acute angle.

17. The lid member according to claim 15, wherein the outer peripheral edge comprises a chamfer at least partially forming the gap.

* * * * *